US012612369B1

(12) United States Patent
Alhumaid

(10) Patent No.: US 12,612,369 B1
(45) Date of Patent: Apr. 28, 2026

(54) ECO-FRIENDLY SYNTHESIS OF A NOVEL NICOTINONITRILE DERIVATIVE (MNPN) WITH ANTIBACTERIAL AND ANTI-INFLAMMATORY ACTIVITIES FOR PREVENTING PRESSURE ULCERS IN INDIVIDUALS WITH DISABILITIES

(71) Applicant: KING FAISAL UNIVERSITY, Al-Ahsa (SA)

(72) Inventor: Majed Mohammed Ali Alhumaid, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 19/420,102

(22) Filed: Dec. 15, 2025

(51) Int. Cl.
*C07D 213/85* (2006.01)
*A61K 31/4418* (2006.01)
*A61P 31/04* (2006.01)
*A61P 31/10* (2006.01)

(52) U.S. Cl.
CPC ........ *C07D 213/85* (2013.01); *A61K 31/4418* (2013.01); *A61P 31/04* (2018.01); *A61P 31/10* (2018.01)

(58) Field of Classification Search
CPC .................................................... C07D 213/85
USPC ......................................................... 514/345
See application file for complete search history.

(56) References Cited

U.S. PATENT DOCUMENTS

| | | | |
|---|---|---|---|
| 8,039,450 | B2 | 10/2011 | Akama et al. |
| 8,344,010 | B2 | 1/2013 | Lingram et al. |
| 8,461,336 | B2 | 6/2013 | Zhou et al. |
| 9,789,116 | B2 | 10/2017 | Markowitz et al. |
| 12,336,982 | B2 | 6/2025 | Markowitz et al. |
| 2004/0142978 | A1 | 7/2004 | Anderson et al. |

FOREIGN PATENT DOCUMENTS

| | | | |
|---|---|---|---|
| WO | 2010018458 | A2 | 2/2010 |
| WO | 2015059618 | A1 | 4/2015 |

OTHER PUBLICATIONS

Haleem et al., Bioorganic Chemistry, 103 (2020), 104222.*

Anwar, Manal., et al., "A Review on The Chemistry of Nicotinonitriles and Their applications", The Egyptian Journal of Chemistry, 2021, DOI:10.21608/EJCHEM.2021.64971.3392. Abstract.

Raghunath B. Toche, et al., "Synthesis of nicotinonitrile derivatives and study of their photophysical properties". Monatsh Chem 142, 261-269 (2011). DOI: https://doi.org/10.1007/s00706-011-0453-2. Abstract.

Jianqiang Wang, et al., Novel 4-Aryl-2-amino-6-(naphthalene-1-yl)-3-cyanopyridine Derivates as Potential Organic Fluorescent Materials Prepared Under Microwave Irradiation via Three-Component Domino Reactions, Synthetic Communications, 44(15), pp. 2205-2214 (2014). DOI: https://doi.org/10.1080/00397911.2014.891239. Abstract.

Wei Mao, et al., 2-Amino-6-(naphthalen-1-yl)-4-phenyl-pyridine-3-carbonitrile, Acta crystallographica. Section E, Structure reports online vol. 67, Pt 4 (2011): o853. doi:10.1107/S1600536811002765. Abstract.

* cited by examiner

*Primary Examiner* — Niloofar Rahmani
(74) *Attorney, Agent, or Firm* — Nath, Goldberg & Meyer; Joshua B. Goldberg

(57) ABSTRACT

A compound 4-(4-methoxyphenyl)-6-(1-naphthyl)-2-propoxy-nicotinonitrile compound, its synthesis, and its use as an antimicrobial and/or anti-inflammatory agent.

11 Claims, 2 Drawing Sheets

ECO-FRIENDLY SYNTHESIS OF A NOVEL NICOTINONITRILE DERIVATIVE (MNPN) WITH ANTIBACTERIAL AND ANTI-INFLAMMATORY ACTIVITIES FOR PREVENTING PRESSURE ULCERS IN INDIVIDUALS WITH DISABILITIES

BACKGROUND

1. Field

The present disclosure relates to the compound 4-(4-methoxyphenyl)-6-(1-naphthyl)-2-propoxy-nicotinonitrile (MNPN), and its synthesis, and its use as an antibacterial and/or anti-inflammatory agent.

2. Description of the Related Art

There remains an ongoing need for new therapeutically active agents for treating a variety of diseases, disorders, and conditions including, but not limited to, various forms of various microbial infections, and the like.

Further, pressure-induced skin ulcers, commonly known as pressure sores or bedsores, represent a significant health challenge for individuals with limited mobility, particularly those with physical disabilities who rely on wheelchairs for daily movement. These conditions may also affect athletes, especially wheelchair users such as basketball players—who remain seated for extended periods during training and competition. Prolonged sitting or immobility leads to continuous pressure on specific areas of the body, impairing blood circulation and causing tissue necrosis. The resulting ulcers not only cause chronic pain and infections, but also increase the risk of severe complications, thereby reducing quality of life and increasing medical care costs. Despite the availability of topical treatments, many current formulations rely on synthetic chemical compounds that often cause skin irritation, have limited antimicrobial efficiency, or exhibit poor biodegradability, leading to negative environmental effects.

To address these limitations, there is a growing need for the development of eco-friendly therapeutic compounds that are both effective and safe for repeated use on sensitive skin.

Thus, new molecules, having the desired therapeutic activities and solving the aforementioned problems are desired.

SUMMARY

The present subject matter relates to a novel nicotinonitrile derivative, 4-(4-methoxyphenyl)-6-(1-naphthyl)-2-propoxy-nicotinonitrile (MNPN) and synthesis thereof. The nicotinonitrile derivative provides potent antibacterial, anti-inflammatory, and antioxidant properties. The compound was synthesized via a four-component reaction of 1-acetonaphthone, 4-anisaldehyde, and malononitrile in the presence of sodium n-propoxide, which acts as both a reactant and a basic catalyst. Ultrasonic irradiation was used as an eco-friendly heating source, providing a sustainable alternative to conventional thermal methods.

In an embodiment, the present subject matter relates to a 4-(4-methoxyphenyl)-6-(1-naphthyl)-2-propoxy-nicotinonitrile compound having a formula I:

I

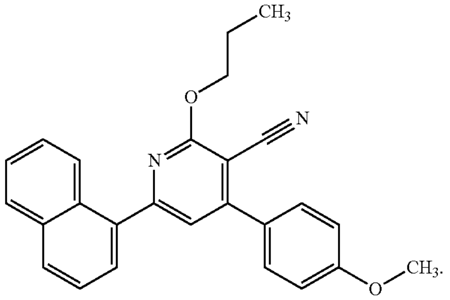

In another embodiment, the present subject matter relates to a pharmaceutically acceptable composition comprising a therapeutically effective amount of the 4-(4-methoxyphenyl)-6-(1-naphthyl)-2-propoxy-nicotinonitrile compound and a pharmaceutically acceptable carrier.

In a further embodiment, the present subject matter relates to a method of treating inflammation in a patient comprising administering to a patient in need thereof a therapeutically effective amount of the 4-(4-methoxyphenyl)-6-(1-naphthyl)-2-propoxy-nicotinonitrile compound.

In a still further embodiment, the present subject matter relates to a method of preventing pressure ulcers in a patient comprising administering to a patient in need thereof a therapeutically effective amount of the 4-(4-methoxyphenyl)-6-(1-naphthyl)-2-propoxy-nicotinonitrile compound.

In another embodiment, the present subject matter relates to a method of treating a microbial infection in a patient comprising administering to a patient in need thereof a therapeutically effective amount of the 4-(4-methoxyphenyl)-6-(1-naphthyl)-2-propoxy-nicotinonitrile compound.

In one more embodiment, the present subject matter relates to a method of making the 4-(4-methoxyphenyl)-6-(1-naphthyl)-2-propoxy-nicotinonitrile compound, the method comprising: adding 1-acetonaphthone, 4-anisaldehyde, sodium n-propoxide, and malononitrile to obtain a reaction mixture; placing the reaction mixture in a closed vessel and exposing the reaction mixture to ultrasound irradiation; cooling the reaction mixture to room temperature; collecting and washing a formed precipitate; purifying the formed precipitate by recrystallization using ethanol; and obtaining the 4-(4-methoxyphenyl)-6-(1-naphthyl)-2-propoxy-nicotinonitrile compound.

These and other features of the present subject matter will become readily apparent upon further review of the following specification.

DETAILED DESCRIPTION OF THE PREFERRED EMBODIMENTS

Figure 1:
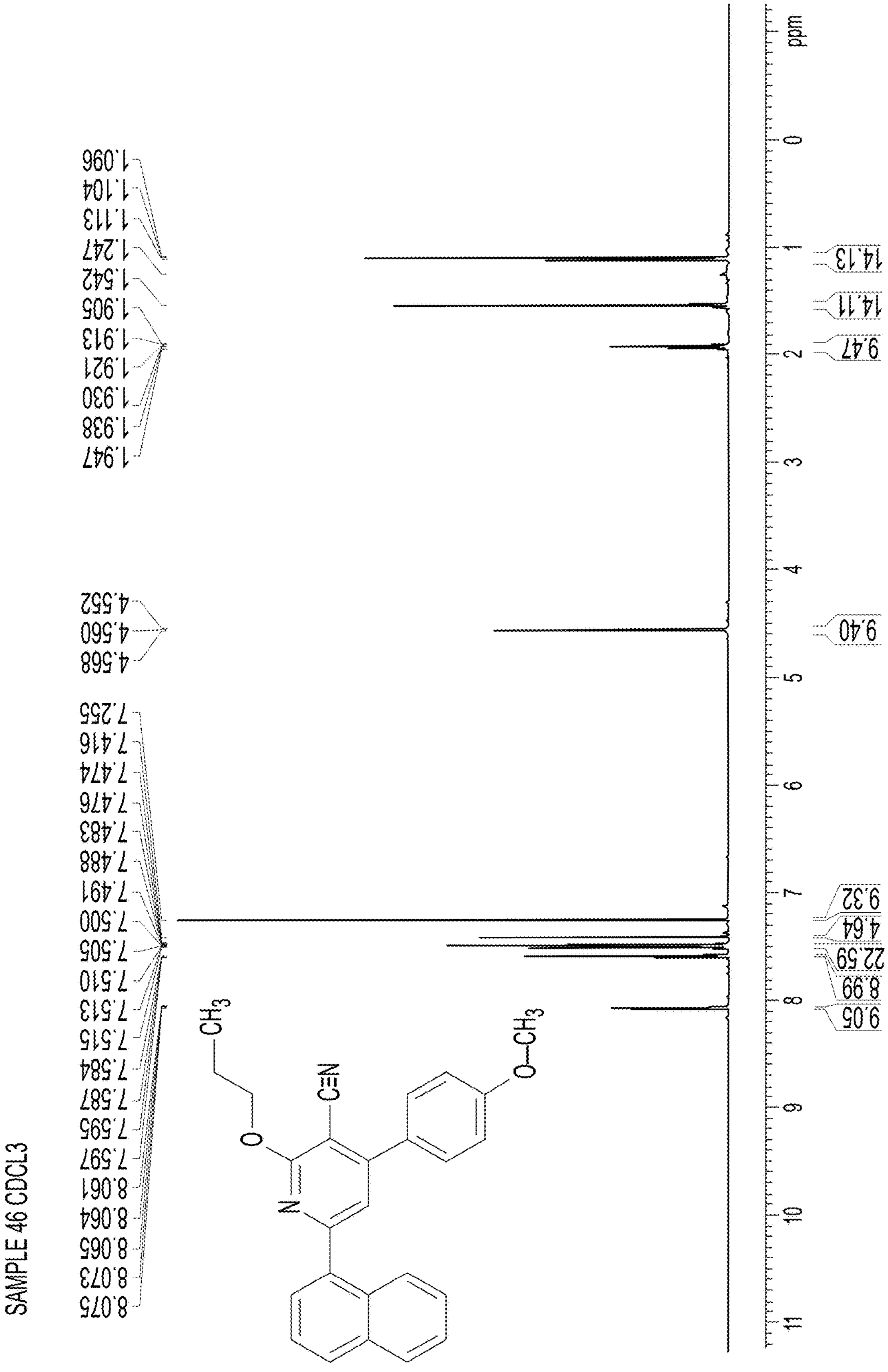
FIG. 1 shows a $^{1}H$ NMR analysis of the 4-(4-methoxyphenyl)-6-(1-naphthyl)-2-propoxy-nicotinonitrile compound.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as inflammation, bacterial infections, or pressure ulcers.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

A pyridine moiety is fundamental heterocyclic fragment of many naturally occurring biomolecules and synthetic compounds. Within the last few decades, many efforts have been made to design diverse synthetic approaches for pyridine derivatives. Among a wide range of pyridines, cyanopyridines acquired special attention due to their great therapeutic importance. They act as anticonvulsant, antihypertensive, anti-inflammatory, antimicrobial, antiviral, antibacterial, anti-Alzheimer, antihistamine, and antitumor drugs.

From an environmental and economic perspective, it is clear that the traditional methods of chemical synthesis are unsustainable and must be changed. Multicomponent coupling reactions provide a solution because they are more cost effective, efficient, and less wasteful than traditional methods. Microwave (MW) provides a powerful tool for synthetic chemistry in light of the current paradigm shift to "green chemistry." Not only can it reduce chemical reaction times from hours to minutes but it can also reduce side reactions, increase yields, and enhance reproducibility compared with conventional heating conditions. According to current synthetic requirements, environmentally benign multicomponent procedures employing MW methodology are particularly welcome.

During ultrasound irradiation, chemical transformations occur, with higher yields and purity of the products, shorter reaction times and milder conditions, that create economic advantages. This greener method, such as ultrasound technique is crucial to reducing the negative impact of traditional methods. Moreover, ultrasound technique is a green chemistry technique that is quicker and healthier than conventional methods.

In light of the multifold properties exhibited by cyanopyridines, the use of multi-component reactions (MCRs) and ultrasonic heating are presented herein. An eco-friendly method for synthesis of new polyfunctionalized 4-(4-methoxyphenyl)-6-(1-naphthyl)-2-propoxy-nicotinonitrile (4) via the four components reaction of 1-acetonaphthone (1), 4-anisaldehyde (2), malononitrile (3) in the presence of sodium n-propoxide as a reactant and basic catalyst, using ultrasound radiation as a source of heat as an eco-friendly method is presented herein.

The present subject matter relates to the synthesis of a novel nicotinonitrile derivative, 4-(4-methoxyphenyl)-6-(1-naphthyl)-2-propoxy-nicotinonitrile (MNPN), designed to provide potent antibacterial, anti-inflammatory, and antioxidant properties. The compound can be synthesized via a four-component reaction of 1-acetonaphthone, 4-anisaldehyde, and malononitrile in the presence of sodium n-propoxide, which acts as both a reactant and basic catalyst. Ultrasonic irradiation can be used as an eco-friendly heating source, providing a sustainable alternative to conventional thermal methods.

Figure 2:
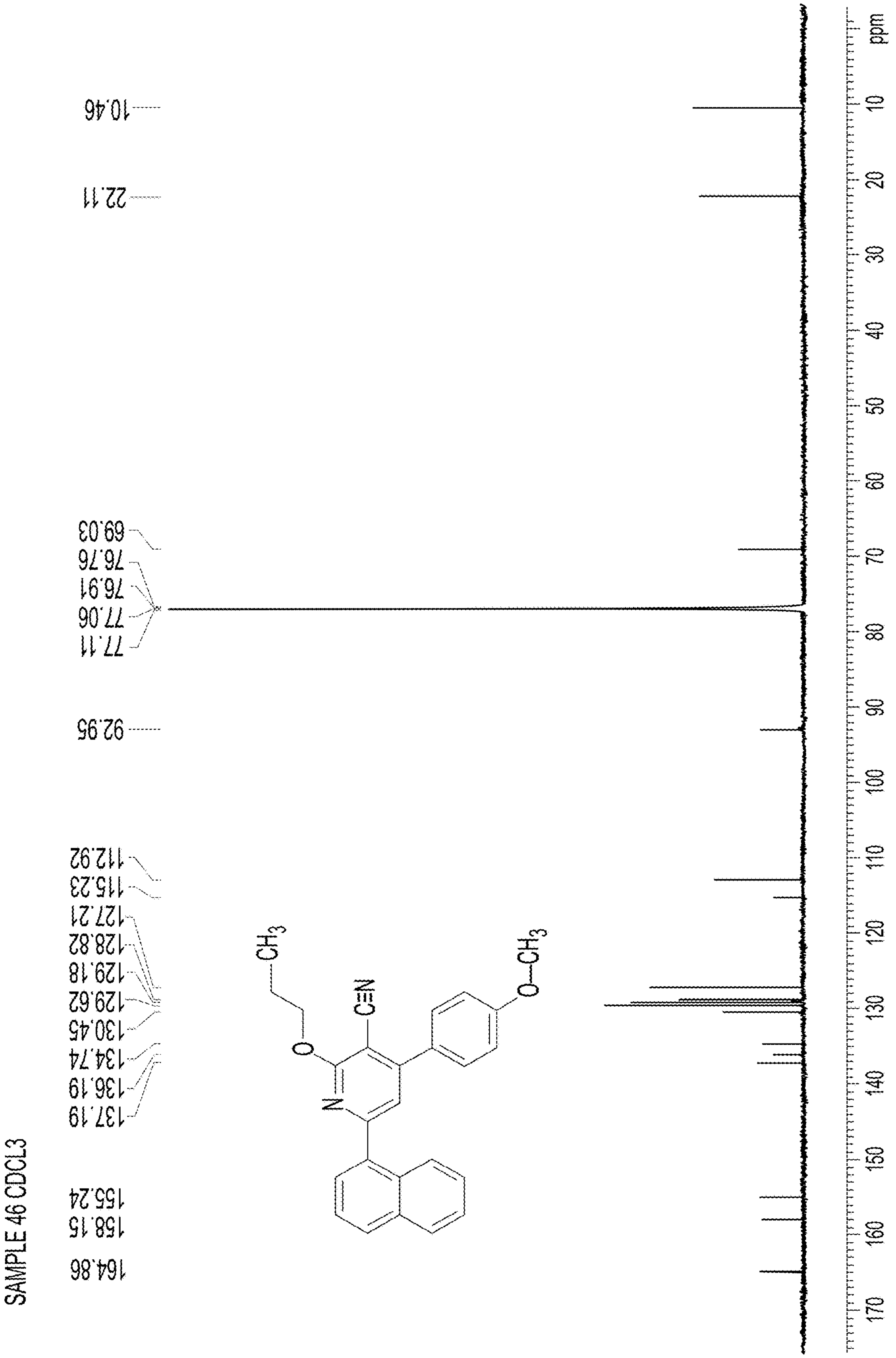
FIG. 2 shows a $^{13}C$ NMR analysis of the 4-(4-methoxyphenyl)-6-(1-naphthyl)-2-propoxy-nicotinonitrile compound.

The chemical structure of the synthesized MNPN was confirmed using spectral analyses (IR, NMR) and elemental analysis, demonstrating the successful formation of the target compound (FIGS. 1 and 2). The MNPN exhibits strong antioxidants, antibacterial, and anti-inflammatory activities, making it a promising candidate for the prevention and treatment of pressure ulcers in individuals with disabilities. Its environmentally friendly synthesis, combined with high biological efficacy, supports the development of safer and more effective topical applications for long-term skin protection, while minimizing ecological impact.

In an embodiment, the present subject matter relates to a 4-(4-methoxyphenyl)-6-(1-naphthyl)-2-propoxy-nicotinonitrile compound having the formula I:

I

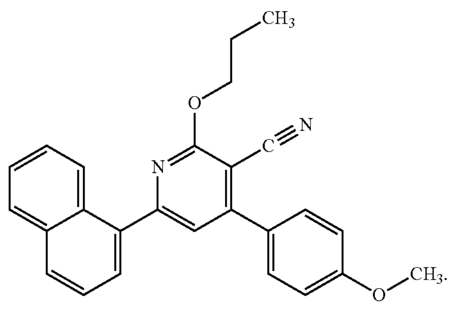

In certain embodiments, the 4-(4-methoxyphenyl)-6-(1-naphthyl)-2-propoxy-nicotinonitrile compound can be obtained as crystals.

In another embodiment, the present subject matter relates to a pharmaceutically acceptable composition comprising a therapeutically effective amount of the 4-(4-methoxyphenyl)-6-(1-naphthyl)-2-propoxy-nicotinonitrile compound and a pharmaceutically acceptable carrier.

In this regard, the present subject matter is further directed to pharmaceutical compositions comprising a therapeutically effective amount of the compound as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises the present compound together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compound is typically administered at a therapeutically or pharmaceutically effective dosage, e.g., a dosage sufficient to provide treatment for an ulcer or for a microbial infection. Administration of the compound or pharmaceutical compositions thereof can be by any method that delivers the compound systemically and/or locally. These methods include oral routes, topical routes, parenteral routes, intraduodenal routes, and the like.

While human dosage levels have yet to be optimized for the present compound, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compound for treating or preventing an ulcer, e.g., a pressure ulcer, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electro transport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present compound, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be like and by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredients of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

In a further embodiment, the present subject matter relates to a method of treating inflammation in a patient comprising administering to a patient in need thereof a therapeutically effective amount of the 4-(4-methoxyphenyl)-6-(1-naphthyl)-2-propoxy-nicotinonitrile compound.

In certain embodiments, the present subject matter relates to a method of preventing pressure ulcers in a patient comprising administering to a patient in need thereof a therapeutically effective amount of the 4-(4-methoxyphenyl)-6-(1-naphthyl)-2-propoxy-nicotinonitrile compound.

In additional embodiments, the present subject matter relates to a method of treating a microbial infection in a patient comprising administering to a patient in need thereof a therapeutically effective amount of the 4-(4-methoxyphenyl)-6-(1-naphthyl)-2-propoxy-nicotinonitrile compound.

In certain embodiments in this regard, the microbial infection can be caused by one or more bacteria or fungi.

In an embodiment, the microbial infection can be caused by one or more gram positive bacteria. In this regard, non-limiting examples of the one or more gram positive bacterial strains causing the microbial infection include *Bacillus cereus* and *Staphylococcus aureus*. In another embodiment, the microbial infection can be caused by one or more gram negative bacteria. In this regard, non-limiting examples of the one or more gram-negative bacterial strains causing the microbial infection include *Pseudomonas aeruginosa* and *Escherichia coli*. In a further embodiment, the microbial infection can be caused by one or more fungi.

In this regard, non-limiting examples of the one or more fungi causing the microbial infection include *Aspergillus flavus* and *Chrysosporium keratinophilum*. Any combination of any of the foregoing are further contemplated herein.

In one more embodiment, the present subject matter relates to a method of making the 4-(4-methoxyphenyl)-6-(1-naphthyl)-2-propoxy-nicotinonitrile compound, the method comprising: adding 1-acetonaphthone, 4-anisaldehyde, sodium n-propoxide, and malononitrile to obtain a reaction mixture; placing the reaction mixture in a closed vessel and exposing the reaction mixture to ultrasound irradiation; cooling the reaction mixture to room temperature; collecting and washing a formed precipitate; purifying the formed precipitate by recrystallization using ethanol; and obtaining the -(4-methoxyphenyl)-6-(1-naphthyl)-2-propoxy-nicotinonitrile compound.

The present production methods can be further seen by referring to the following Scheme 1:

Scheme 1

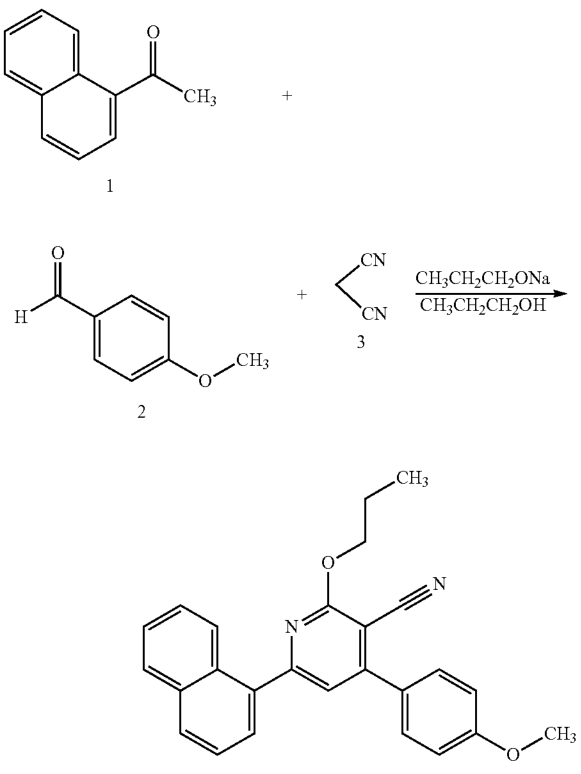

1 2 3 4

In an embodiment of the present production methods, the 1-acetonaphthone and the 4-anisaldehyde may be mixed together to form a mixture before adding to the sodium n-propoxide.

In another embodiment of the present production methods, the 1-acetonaphthone, the 4-anisaldehyde, and the sodium n-propoxide are stirred at room temperature for 20 minutes.

In a further embodiment of the present production methods, malononitrile is added to a mixture of 1-acetonaphthone, 4-anisaldehyde, and sodium n-propoxide.

In an embodiment of the present production methods, the 1-acetonaphthone, the 4-anisaldehyde, and the malonitrile are added in a 1:1:1 molar ratio.

In an additional embodiment of the present production methods, the sodium n-propoxide can include about 0.30 g of sodium in about 50 mL of absolute ethanol.

In another embodiment, the reaction mixture was exposed to ultrasound irradiation for about 3 hours at a temperature of about 50° C. in a sonicator.

In still another embodiment, the formed precipitate is washed with water.

The following examples relate to various methods of manufacturing the specific compounds and application of the same, as described herein. All compound numbers expressed herein are with reference to the synthetic pathway figures shown above.

EXAMPLES

Example 1

Synthesis of 4-(4-methoxyphenyl)-6-(1-naphthyl)-2-propoxy-nicotinonitrile (4)

A mixture of 1-acetonaphthone (1.70 g, 0.01 mol) and 4-anisaldehyde (1.36 g, 0.010) was added to sodium n-propoxide solution (0.30 g of sodium in 50 mL of absolute ethanol) and stirred for 20 min at room temperature, then malononitrile (0.66 g 0.010 mol) was added and the reaction mixture was placed in a closed vessel and exposed to ultrasound irradiation for about 3 hours at 50° C. in a sonicator. After completion of the reaction (monitored with TLC), the reaction mixture was then cooled to room temperature. The formed precipitate was collected by filtration, washed by distilled water, dried and crystallized from ethanol to give the desired product 4-(4-methoxyphenyl)-6-(1-naphthyl)-2-propoxy-nicotinonitrile (4).

Example 2

In Vitro Antimicrobial activity

To assess the potential biological applications of the newly synthesized compound, their antibacterial and antifungal activities were evaluated against various bacterial and fungal strains, including *P. aeruginosa, S. aureus, E. coli, A. flavus, B. cereus, C. albicans*, and *T. rubrum*. The biological activity of the compound was determined by measuring the diameter of the inhibition zone, which reflects the compound's effectiveness in suppressing microbial growth. The results, summarized in Table 1, reveal that the MNPN compound exhibited the largest inhibition zone and the lowest minimum inhibitory concentration (MIC), indicating superior antimicrobial potency. Furthermore, Table (1) presents a comparison of the inhibition zone values of the identified MNPN compound with those of the antibiotic chloramphenicol, which possesses a high activity index and is therefore expected to exhibit a large inhibition zone. The MNPN compound showed notable antibacterial activity against *E. coli, P. aeruginosa, S. aureus*, and *B. cereus*, with activity indexes of 64.55, 73.11, 76.89, and 73.11, respectively). Additionally, they demonstrated promising antifungal effects against *A. flavus, T. rubrum*, and *C. albicans*, with activity indexes of 64.01, 58.68, and 60.94, respectively.

TABLE 1

| Antibacterial and antifungal activities of the MNPN compound expressed as inhibition zone (IZ, mm) and activity index (%). | | |
|---|---|---|
| Anti-bacterial activity | | |
| Bacterial strains | Parameters | MNPN |
| *Pseudomonas aeruginosa* | IZ | 14.1 |
| | % | 73.11 |
| | MIC | 7.12 |
| *Escherichia coli* (−ve) | IZ | 14.01 |
| | % | 64.55 |
| | MIC | 2.95 |
| *Staphylococcus aureus* (+ve) | IZ | 15.4 |
| | % | 76.89 |
| | MIC | 7.25 |
| *Bacillus cereus* (+ve) | IZ | 13.2 |
| | % | 73.11 |
| | MIC | 6.32 |
| Anti-fungal activity | | |
| fungal strains | Parameters | MNPN |
| *Aspergillus flavus* | IZ | 11.87 |
| | % | 64.01 |
| | MIC | 6.74 |
| *Trichophyton rubrum* | IZ | 13.24 |
| | % | 58.68 |
| | MIC | 6.31 |
| *Candida albicans* | IZ | 13.21 |
| | % | 60.94 |
| | MIC | 6.15 |

It is to be understood that the 4-(4-methoxyphenyl)-6-(1-naphthyl)-2-propoxy-nicotinonitrile compound, compositions containing the same, and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A 4-(4-methoxyphenyl)-6-(1-naphthyl)-2-propoxy-nicotinonitrile compound having a formula I:

I

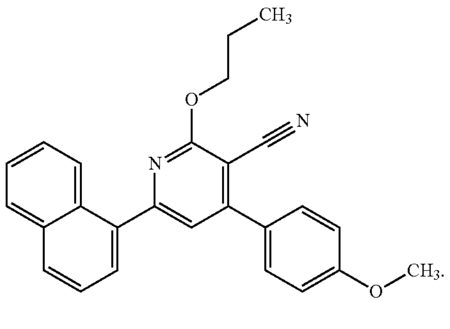

2. The 4-(4-methoxyphenyl)-6-(1-naphthyl)-2-propoxy-nicotinonitrile compound of claim 1, wherein the compound is in crystal form.

3. A pharmaceutically acceptable composition comprising a therapeutically effective amount of the 4-(4-methoxyphenyl)-6-(1-naphthyl)-2-propoxy-nicotinonitrile compound of claim 1 and a pharmaceutically acceptable carrier.

4. A method of making the 4-(4-methoxyphenyl)-6-(1-naphthyl)-2-propoxy-nicotinonitrile compound of claim 1, the method comprising:

adding 1-acetonaphthone, 4-anisaldehyde, sodium n-propoxide, and malononitrile to obtain a reaction mixture;

placing the reaction mixture in a closed vessel and exposing the reaction mixture to ultrasound irradiation;

cooling the reaction mixture to room temperature;

collecting and washing a formed precipitate;

purifying the formed precipitate by recrystallization using ethanol; and obtaining the -(4-methoxyphenyl)-6-(1-naphthyl)-2-propoxy-nicotinonitrile compound.

5. The method of making the 4-(4-methoxyphenyl)-6-(1-naphthyl)-2-propoxy-nicotinonitrile compound of claim 4, wherein the 1-acetonaphthone and the 4-anisaldehyde are mixed together before adding to the sodium n-propoxide.

6. The method of making the 4-(4-methoxyphenyl)-6-(1-naphthyl)-2-propoxy-nicotinonitrile compound of claim 4, wherein the 1-acetonaphthone, the 4-anisaldehyde, and the sodium n-propoxide are stirred at room temperature for 20 minutes.

7. The method of making the 4-(4-methoxyphenyl)-6-(1-naphthyl)-2-propoxy-nicotinonitrile compound of claim 4, wherein malononitrile is added to the mixture of the 1-acetonaphthone, the 4-anisaldehyde, and the sodium n-propoxide.

8. The method of making the 4-(4-methoxyphenyl)-6-(1-naphthyl)-2-propoxy-nicotinonitrile compound of claim 4, wherein the 1-acetonaphthone, the 4-anisaldehyde, and the malonitrile are added in a 1:1:1 molar ratio.

9. The method of making the 4-(4-methoxyphenyl)-6-(1-naphthyl)-2-propoxy-nicotinonitrile compound of claim 4, wherein the sodium n-propoxide comprises 0.30 g of sodium in 50 mL of absolute ethanol.

10. The method of making the 4-(4-methoxyphenyl)-6-(1-naphthyl)-2-propoxy-nicotinonitrile compound of claim 4, wherein the reaction mixture was exposed to ultrasound irradiation for at least about 3 hours at a temperature of at least about 50° C. in a sonicator.

11. The method of making the 4-(4-methoxyphenyl)-6-(1-naphthyl)-2-propoxy-nicotinonitrile compound of claim 4, wherein the formed precipitate is washed with water.

* * * * *